United States Patent
Cheng et al.

(10) Patent No.: US 7,144,419 B2
(45) Date of Patent: Dec. 5, 2006

(54) DRUG-POLYMER COATED STENT WITH BLENDED PHENOXY AND STYRENIC BLOCK COPOLYMERS

(75) Inventors: Peiwen Cheng, Santa Rosa, CA (US); Kishore Udipi, Santa Rosa, CA (US); Kaushik Patel, Windsor, CA (US); Rangarajan Sundar, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 362 days.

(21) Appl. No.: 10/351,136

(22) Filed: Jan. 24, 2003

(65) Prior Publication Data

US 2004/0148002 A1     Jul. 29, 2004

(51) Int. Cl.
A61F 2/06    (2006.01)
A61F 2/00    (2006.01)
A61L 33/00   (2006.01)
B05D 3/00    (2006.01)

(52) U.S. Cl. .................. 623/1.11; 623/1.15; 623/1.19; 623/1.42; 623/1.46; 424/425

(58) Field of Classification Search .............. 623/1.11, 623/1.13, 1.42, 1.43, 1.12, 1.14, 1.15, 1.16, 623/1.17, 1.18, 1.19, 1.2, 1.21, 1.22, 1.46; 427/2.24, 2.25; 424/422, 423, 424, 425, 424/426
See application file for complete search history.

(56) References Cited

U.S. PATENT DOCUMENTS

| | | | |
|---|---|---|---|
| 4,196,065 A | 4/1980 | Gaussens et al. | |
| 4,929,510 A | 5/1990 | Ruckenstein et al. | |
| 5,545,208 A * | 8/1996 | Wolff et al. | 623/1.22 |
| 5,980,972 A | 11/1999 | Ding | |
| 6,214,901 B1 | 4/2001 | Chudzik et al. | |
| 6,270,788 B1 | 8/2001 | Koulik et al. | |
| 6,451,050 B1 * | 9/2002 | Rudakov et al. | 623/1.15 |
| 6,712,842 B1 * | 3/2004 | Gifford et al. | 623/1.13 |
| 6,753,071 B1 * | 6/2004 | Pacetti | 428/212 |
| 6,835,387 B1 * | 12/2004 | Herrmann | 424/425 |
| 2001/0014717 A1 * | 8/2001 | Hossainy et al. | 525/60 |
| 2002/0107330 A1 | 8/2002 | Kalpana et al. | |
| 2003/0208259 A1 * | 11/2003 | Penhasi | 623/1.15 |

FOREIGN PATENT DOCUMENTS

| | | |
|---|---|---|
| WO | WO 00/32255 A1 | 6/2000 |
| WO | WO 02/055122 A1 | 7/2002 |

OTHER PUBLICATIONS

Sue-Hua Chen, et al., "In Situ Compatibilized Polymer Blends of Phenoxy and ABS", Journal of Applied Polymer Science, John Wiley and Sons, Inc., New York, US, vol. 51, No. 5, Jan. 31, 1994, pp. 955-965.

* cited by examiner

Primary Examiner—Corrine McDermott
Assistant Examiner—Thomas J. Sweet

(57) ABSTRACT

The present invention provides a system for treating a vascular condition, including a catheter, a stent coupled to the catheter, a drug-polymer coating on the stent including a polymeric blend of a phenoxy polymer and a styrenic block copolymer, and a bioactive drug dispersed within the drug-polymer coating.

22 Claims, 5 Drawing Sheets

300

400

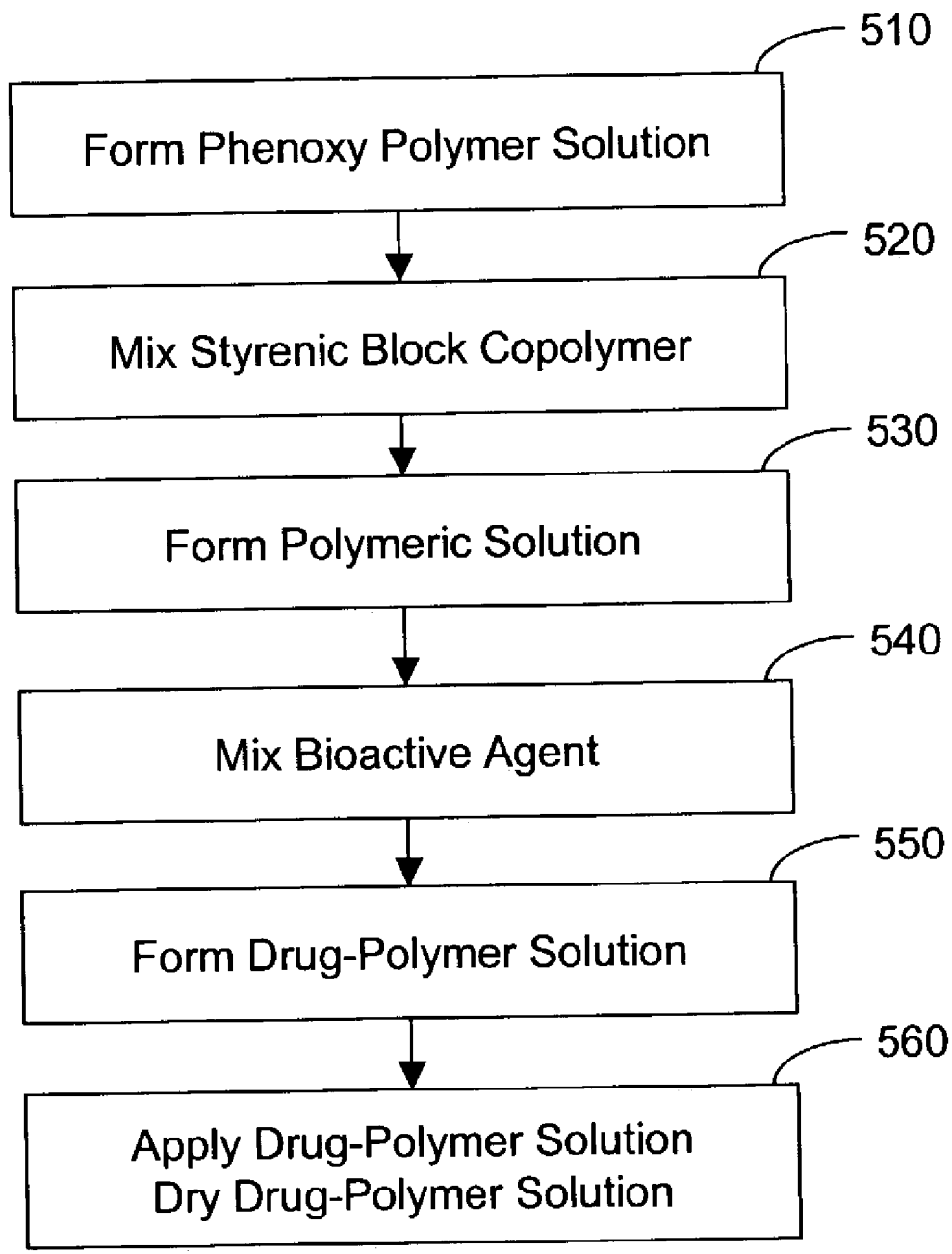

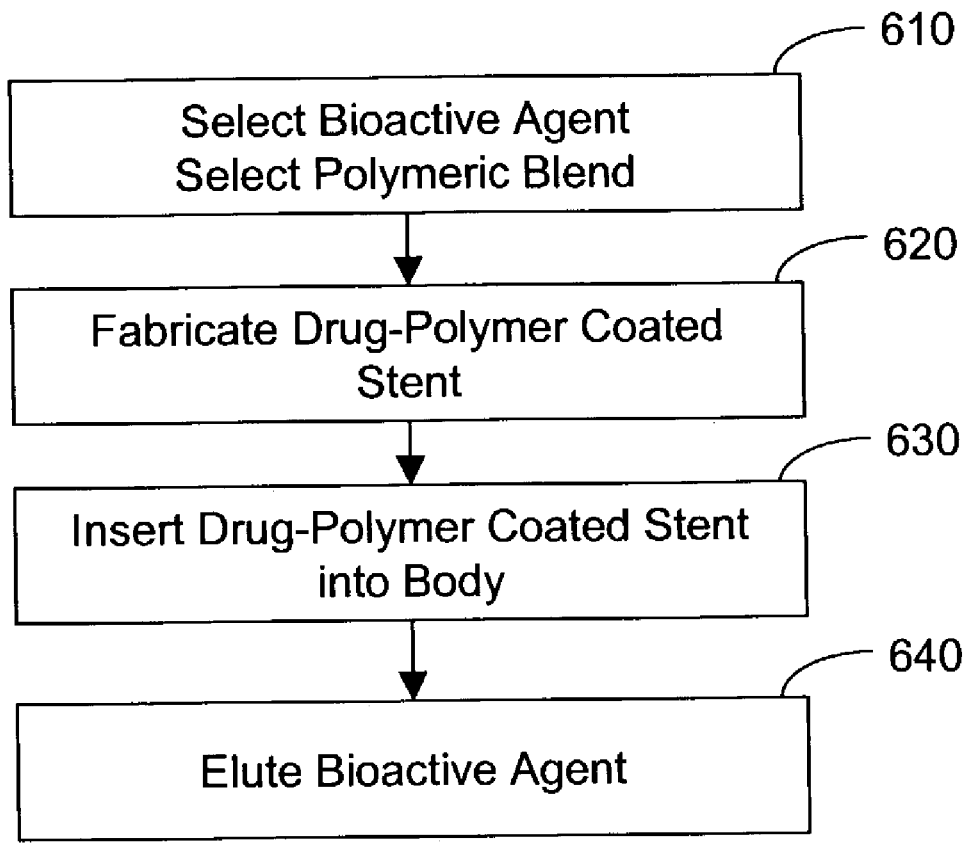

DRUG-POLYMER COATED STENT WITH BLENDED PHENOXY AND STYRENIC BLOCK COPOLYMERS

FIELD OF THE INVENTION

This invention relates generally to biomedical stents. More specifically, the invention relates to a drug-polymer coating comprising a polymeric blend of a phenoxy polymer and a styrenic block copolymer with a dispersed bioactive drug on an endovascular stent for in vivo, timed-release drug delivery.

BACKGROUND OF THE INVENTION

Much medical research and development in the last decade has been dedicated to stents, and in the most recent years, to drug coatings for stents. The efficacy of vascular stents is potentially increased by the addition of stent coatings that contain pharmaceutical drugs. These drugs may be released from the coating while in the body, delivering their patent effects at the site where they are most needed. Thus, the localized levels of the medications can be elevated, and therefore potentially more effective than orally- or intravenously-delivered drugs that distribute throughout the body, the latter which may have little effect on the impacted area, or which may be expelled rapidly from the body without achieving their pharmaceutical intent. Furthermore, drugs released from tailored stent coatings may have controlled, timed-release qualities, eluting their bioactive agents over hours, weeks or even months. In selecting polymers for drug delivery, three important criteria must be met: polymer biocompatibility, satisfactory mechanical properties such as durability and integrity during roll down and expansion of the stent, and correct release profiles for the drugs.

Certain classes of drug-polymer chemistries have been explored in current art. A composition with a bioactive agent for coating the surface of a medical device based on poly (alkyl)(meth)acrylate and poly(ethyline-co-vinyl acetate) is described in "Bioactive Agent Release Coating," Chudzik, et al., U.S. Pat. No. 6,214,901, issued Apr. 10, 2001. A composite polymer coating with a bioactive agent and a barrier coating formed in situ by a low energy plasma polymerization of a monomer gas is described in "Polymeric Coatings with Controlled Delivery of Active Agents," K. R. Kamath, publication WO 00/32255, published Jun. 8, 2000. A polymeric coating for an implantable medical article based on hydrophobic methacrylate and acrylate monomers, a functional monomer having pendant chemically reactive amino groups capable of forming covalent bonds with biologically active compounds, and a hydrophilic monomer wherein a biomolecule is coupled to the coated surface, is presented in "Implantable Medical Device," E. Koulik, et al., U.S. Pat. No. 6,270,788, issued Aug. 7, 2001. Use of block copolymers on a hydrophobic polymer substrate is described in "Biocompatible Polymer Articles," E. Ruckenstein, et al., U.S. Pat. No. 4,929,510, issued May 29, 1990. A method for the columetic inclusion and grafting of hydrophilic compounds in a hydrophobic substrate using an irradiation means is described in "Hydrophobic Substrate with Grafted Hydrophilic Inclusions," G. Gaussens, et al., U.S. Pat. No. 4,196,065, issued Apr. 1, 1980.

Unfortunately, some drug polymers do not provide the mechanical flexibility necessary to be effectively used on a stent. A stent may be deployed by self-expansion or balloon expansion, accompanied by a high level of bending at portions of the stent framework that can cause cracking, flaking, peeling, or delaminating of many candidate drug polymers while the stent diameter is increased by threefold or more during expansion. The candidate drug polymer may not stick or adhere, or it may elute its pharmacologically active constituents too slowly or too quickly, possibly in a toxic manner. One drug can elute much faster than a second drug in the same drug polymer, making the controlled delivery of drugs difficult. If a drug is eluted too quickly, it may be ineffective and possibly toxic. If a drug is eluted too slowly, then its intended effect on the body could be compromised. Furthermore, the coating may fall off, crystallize or melt during preparation and sterilization prior to deployment, further limiting the types of drug polymers acceptable for use on cardiovascular stents.

A drug-polymer system that can be tailored to provide a desired elution rate for a specific drug would be beneficial. It is desirable to have a drug-polymer system that can be tailored to accommodate a variety of drugs for controlled time delivery, while maintaining mechanical integrity during stent deployment. A polymeric system that can be readily altered to control the elution rate of an interdispersed bioactive drug and to control its bioavailability is of further benefit.

It is an object of this invention, therefore, to provide a system for treating heart disease and other vascular conditions, to provide methods of manufacturing drug-polymer coated stents, and to overcome the deficiencies and limitations described above.

SUMMARY OF THE INVENTION

One aspect of the invention provides a system for treating a vascular condition, including a catheter, a stent coupled to the catheter, a drug-polymer coating disposed on the stent framework, and a bioactive drug dispersed within the drug-polymer coating. The drug-polymer coating includes a polymeric blend of a phenoxy polymer and a styrenic block copolymer. The polymeric blend provides a controlled drug-elution characteristic.

Another aspect of the invention is a method of manufacturing a drug-polymer coated stent comprising mixing a phenoxy polymer, a styrenic block copolymer, and a bioactive agent to form a drug-polymer solution, applying the drug-polymer solution onto a stent framework, and drying the drug-polymer solution.

Another aspect of the invention provides a drug-polymer coated stent, comprising a stent framework and a drug-polymer coating disposed on the stent framework, wherein the drug-polymer coating includes a polymeric blend of a phenoxy polymer and a styrenic block copolymer, with a bioactive drug dispersed within the drug-polymer coating. The fractional part of the phenoxy polymer and the styrenic block copolymer is based on a predetermined elution rate of the bioactive drug.

Another aspect of the invention is a method for treating a vascular condition. A drug-polymer coated stent is inserted within the body, wherein the drug-polymer coated stent includes a bioactive agent and a polymeric blend of a phenoxy polymer and a styrenic block copolymer. The elution rate of the bioactive agent into the body is controlled based on the polymeric blend. The polymeric blend is selected based on a predetermined elution rate of the bioactive agent.

BRIEF DESCRIPTION OF THE DRAWINGS

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, wherein:

FIG. 5 is a flow diagram of one embodiment of a method of manufacturing a drug-polymer coated stent, in accordance with the current invention; and FIG. 6 is a flow diagram of one embodiment-of a method of treating a vascular condition, in accordance with the current invention.

DETAILED DESCRIPTION OF THE PRESENTLY PREFERRED EMBODIMENTS

Figure 1:
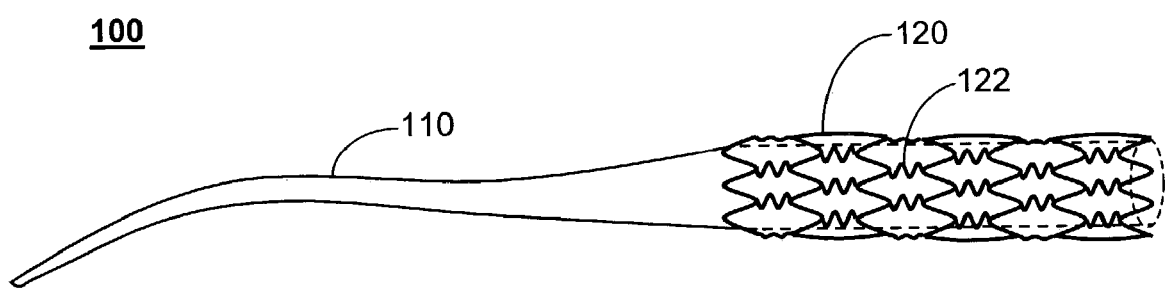
FIG. 1 is an illustration of one embodiment of a system for treating a vascular condition including a catheter, a stent, and a drug-polymer coating disposed on the stent, in accordance with the current invention.

In one embodiment of the present invention, tailoring the fraction of a phenoxy polymer and a styrenic block copolymer in a blended polymer with one or more pharmaceutical drugs controls the elution rate of the drugs from a biomedical stent coated with the drug-polymer.

Blended phenoxy polymers and styrenic block copolymers such as Kraton-G® or Kraton-D® provide coatings with good overall property balance, particularly with respect to durability and drug elution. Phenoxy resins are high molecular weight, linear polymers derived from parent epoxy polymers. They are amorphous, have a relatively high glass transition temperature (Tg), and offer mechanical and barrier properties. Phenoxy resins are also tough and ductile. They are widely used in coatings for food cans and comply with the Food and Drug Administration (FDA) Food Additive Regulations 21 CFR 175.300 and 21 CFR 177.1440. Phenoxy polymers with interdispersed drugs have relatively long elution rates that are not high enough in many cases to effectively dispense the drugs.

Kraton resins are thermoplastic elastomers. Kraton polymers such as Kraton-G® and Kraton-D® are manufactured by Kraton Polymers of Houston, Tex. In terms of molecular structure, Kraton resins are anionically polymerized block copolymers with hydrophobic and hydrophilic phase separation properties. Kraton-G® polymers have a saturated mid-block such as an ethylene and butylene random copolymer or an ethylene and propylene chain. Kraton-D® polymers have an unsaturated rubbery mid-block such as butadiene or isoprene. The rubbery mid-blocks offer good impact resistance properties at low and ambient temperatures. The relatively low glass transition temperature also gives better adhesive properties and relatively fast drug release. In addition, Kraton resins have very good compatibility with a wide range of polymers to allow combinations of properties that could not be achieved otherwise.

By tailoring phenoxy and Kraton blends, desired drug release properties and good mechanical properties can be achieved for use as a coating for blood-contacting biomedical implants such as stents. Metal-adhering attributes such as hydrophilicity aid in the cohesiveness of the polymers to metallic stents, whereas hydrophobic attributes assist in the timed-release control of pharmaceutical compounds interdispersed within the drug-polymer coating. The formulations and fractional composition of the blended polymers may be selected to provide desired elution rates of the embedded bioactive agents.

One aspect of the present invention is a system for treating heart disease, various cardiovascular ailments, and other vascular conditions using catheter-deployed endovascular stents with tailored polymeric coatings for controlling the timed-release properties of interdispersed bioactive agents and drugs. Treatment of vascular conditions may include the prevention or correction of various ailments and deficiencies associated with the cardiovascular system, urinogenital systems, biliary conduits, abdominal passageways and other biological vessels within the body.

One embodiment of the system for treating a vascular condition, in accordance with the present invention, is illustrated in FIG. 1 at 100. In this embodiment, vascular condition treatment system 100 includes a catheter 110, a stent 120 coupled to the catheter, and a drug-polymer coating 122 on the stent or stent framework. Drug-polymer coating 122 includes a polymeric blend of a phenoxy polymer and a styrenic block copolymer, and one or more bioactive agents dispersed throughout the coating. The bioactive agent may be a pharmacologically active drug or bioactive compound. The polymeric blend controls the elution rate of the bioactive agent, and provides a controlled drug-elution characteristic. Drug elution refers to the transfer of the bioactive agent out from drug-polymer coating 122. The elution is determined as the total amount of bioactive agent excreted out of drug-polymer coating 122, typically measured in units of weight such as micrograms, or in weight per peripheral area of the stent. In one embodiment, the polymeric coating includes between 0.5 percent and 50 percent of the bioactive drug or agent by weight.

Upon insertion of catheter 110 and stent 120 with drug-polymer coating 122 into a directed vascular region of a human body, stent 120 may be expanded by applying pressure to a suitable balloon inside the stent, or by retracting a sheath to allow expansion of a self-expanding stent. Balloon deployment of stents and!self-expanding stents are well known in the art. Catheter 110 may include the balloon used to expand stent 120. Catheter 110 may include a sheath that retracts to allow expansion of a self-expanding stent.

Figure 2:
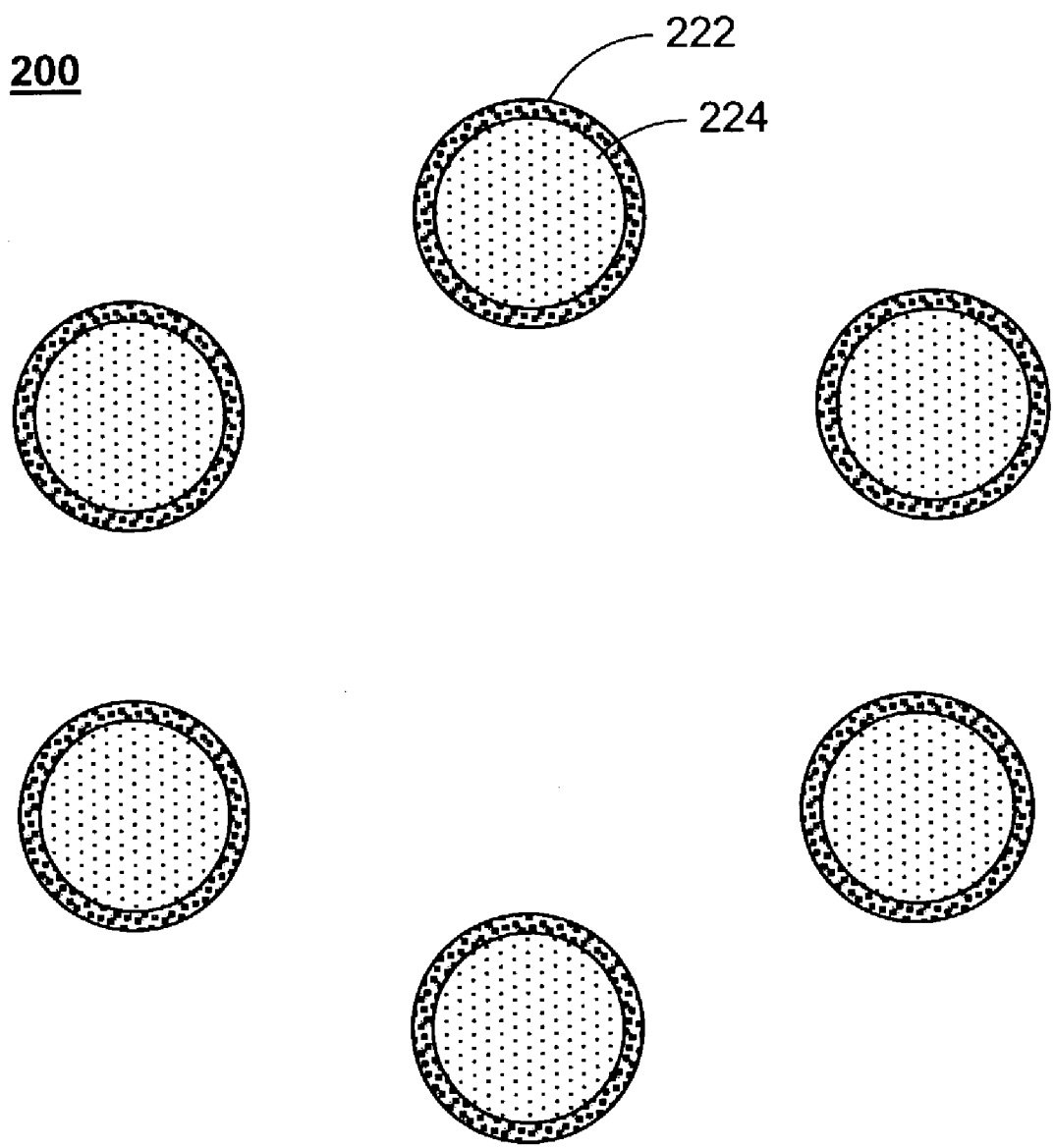
FIG. 2 is a cross-sectional view of one embodiment of a drug-polymer coated stent, in accordance with the current invention.

FIG. 2 shows an illustration of a stent cross-section containing a drug-polymer coating on the stent surface, in accordance with the present invention at 200. Drug-polymer coated stent 200 includes a drug-polymer coating 222 disposed on a stent framework 224. Drug-polymer coating 222 includes a polymeric blend of a phenoxy polymer and a styrenic block copolymer forming a polymeric matrix, with a bioactive drug dispersed within the matrix. Drug-polymer coating 222 may contain one or more pharmaceutical drugs or bioactive agents. Drug-polymer coating 222 may contain a polymeric matrix in which one or more bioactive agents are interdispersed.

Stent framework 224 typically includes a metallic or a polymeric base. The metallic base comprises a metal such as stainless steel, nitinol, tantalum, MP35N alloy, platinum, titanium, a suitable biocompatible alloy, a suitable biocompatible material, or any combination thereof. The polymeric base material is any suitable polymer for biomedical stent applications, as is known in the art.

Drug-polymer coated stent 200 includes one or more polymeric coatings on stent framework 224. A primer coating, adhesive coating or barrier coating can be positioned between drug-polymer coating 222 and stent framework 224.

Drug-polymer coating 222 may have a predominantly hydrophilic characteristic to improve metal adhesion and, in some cases, to enhance the elution of embedded bioactive material. Drug-polymer coating 222 may also have a hydrophobic characteristic. A relatively hydrophobic characteristic usually slows or mitigates the elution of the bioactive agents and polymeric material into the body, and provides a tailored barrier for the elution of bioactive material from the drug-polymer coating.

Drug-polymer coating 222 includes one or more bioactive drugs or agents. The bioactive agent is an agent against one or more conditions including coronary restenosis, cardiovascular restenosis, angiographic restenosis, arteriosclerosis, hyperplasia, and other diseases and conditions. For example, the bioactive agent can be selected to inhibit or prevent vascular restenosis, a condition corresponding to a narrowing or constriction of the diameter of the bodily lumen where the stent is placed. In one embodiment, the bioactive drug comprises an antirestenotic agent. In another embodiment, the bioactive drug comprises a bioactive agent such as an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative. In another embodiment, drug-polymer coating 222 includes a combination or cocktail of pharmaceutical drugs.

A number of pharmaceutical drugs have the potential to be used in drug-polymer coatings. For example, an antirestenotic agent such as rapamycin prevents or reduces the recurrence of narrowing and blockage of the bodily vessel. An antisense drug works at the genetic level to interrupt the process by which disease-causing proteins are produced. An antineoplastic agent is typically used to prevent, kill, or block the growth and spread of cancer cells in the vicinity of the stent. An antiproliferative agent may prevent or stop targeted cells or cell types from growing. An antithrombogenic agent actively retards blood clot formation. An anticoagulant often delays or prevent blood coagulation with anticoagulant therapy, using compounds such as heparin and coumarins. An antiplatelet agent may be used to act upon blood platelets, inhibiting their function in blood coagulation. An antibiotic is frequently employed to kill or inhibit the growth of microorganisms and to combat disease and infection. An anti-inflammatory agent such as dexamethasone can be used to counteract or reduce inflammation in the vicinity of the stent. At times, a steroid is used to reduce scar tissue in proximity to an implanted stent. A gene therapy agent may be capable of changing the expression of a person's genes to treat, cure or ultimately prevent disease.

By definition, a bioactive agent is any therapeutic substance that provides treatment of disease or disorders. An organic drug is any small-molecule therapeutic material. A pharmaceutical compound is any compound that provides a therapeutic effect. A recombinant DNA product or a recombinant RNA product includes altered DNA or RNA genetic material. Bioactive agents of pharmaceutical value may also include collagen and other proteins, saccharides, and their derivatives. The molecular weight of the bioactive agent typically range from 200 to 60,000 Dalton and above.

Drug-polymer coating 222 elutes at least one bioactive agent. Drug-polymer coating 222 may include and elute multiple bioactive agents. Drug-polymer coating 222 can be tailored to control the elution of one or more bioactive agents primarily by diffusion processes. In some cases, a portion of the polymeric coating is absorbed into the body to release bioactive agents from within the coating.

Drug-polymer coating 222 contains a polymeric blend wherein the polymeric blend comprises a fractional part of the styrenic block copolymer based on a predetermined elution rate of the bioactive drug. Modification of the polymeric blend allows, for example, rapid delivery of a pharmacologically active drug or bioactive agent within twenty-four hours of surgery, with a slower, steady delivery of a second bioactive agent over the next three to six months.

Figure 3:
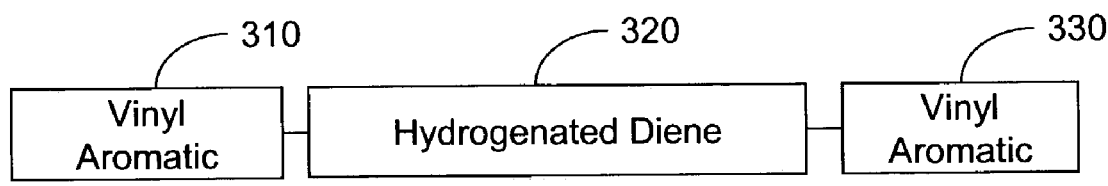
FIG. 3 is a schematic illustration of a styrenic block copolymer, in accordance with the current invention.

FIG. 3 shows a schematic illustration of a styrenic block copolymer, in accordance with the present invention at 300. Styrenic block copolymer 300 has two end-blocks 310, 330 and a mid-block 320. End-blocks 310 and 330 are vinyl aromatics such as styrene, and mid-block 320 that comprises a hydrogenated diene. The hydrogenated diene can be saturated or unsaturated. Styrenic block copolymer 300 may comprise styrene-ethylene/butylene-styrene, where the ethylene/butylene is a random copolymer linear chain. Another example of a styrenic block copolymer with a saturated mid-block is styrene-ethylene/propylene-styrene, where the ethylene/propylene represents a linear copolymer chain between two end-blocks of styrene. Styrenic block copolymer 300 often comprises vinyl aromatic end-blocks 310 and 330 with an unsaturated diene, such as styrene-butadiene-styrene or styrene-isoprene-styrene. The styrene block copolymer has a molecular weight between 20,000 Daltons and 200,000 Daltons, depending on the length of the block copolymer and the desired elution characteristics.

The styrenic block copolymer is combined with the phenoxy polymer to form a blended polymer, also referred to as a polymeric blend. The phenoxy polymer generally has a molecular weight between 20,000 Daltons and 200,000 Daltons. The polymeric blend provides a controlled drug-elution characteristic, with a higher fraction of phenoxy polymer typically corresponding to a lower elution rate, and a higher fraction of styrenic block copolymer corresponding to a higher elution rate of an interdispersed bioactive agent. The polymeric blend may comprise between 10 percent and 90 percent phenoxy polymer by volume. The polymeric blend may comprise between 10 percent and 90 percent styrenic block copolymer by volume.

Figure 4:
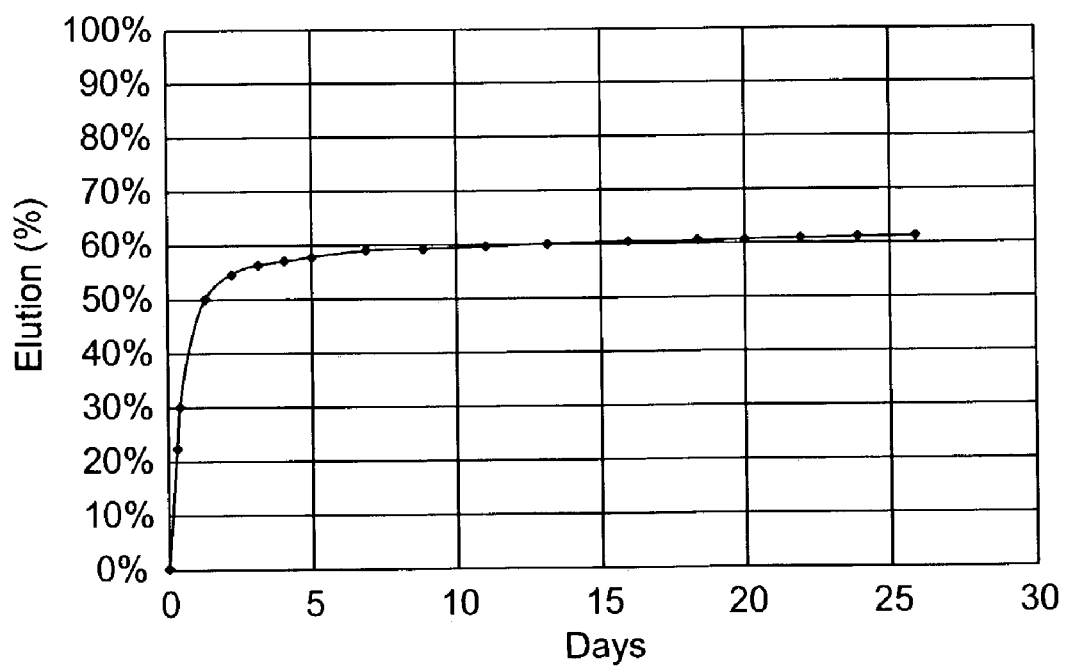
FIG. 4 is a graphical illustration of drug elution from a drug-polymer coated stent with an antirestenotic drug, in accordance with the current invention.

FIG. 4 shows a graphical illustration of the elution of a bioactive agent from a drug-polymer coated stent, in accordance with the present invention at 400. Elution graph 400 shows the elution of an antirestenotic drug from a drug-polymer coated stent as a function of time. The elution of the bioactive agent is indicated as a percentage by weight of total drug dispersed within the stent coating. Typical units used for drug elution include micrograms of drug. Alternatively, they can be normalized to a unit volume with units such as micrograms per cubic centimeter of drug-polymer, or normalized to the periphery area of the stent with units such as micrograms per square centimeter. The elution profile of the drug shows a high rate of drug delivery over an initial period of two days or so after stent deployment, with minimal drug eluted over the remainder of the month. The elution rate is determined from a typical elution graph 400 by taking the derivative with respect to time, or by dividing the total amount of drug eluted by the elapsed time since stent deployment. Selection of the appropriate drug, the fractional portion of the phenoxy polymer and the styrenic block copolymer in the polymeric blend, and the method of preparation establish the elution profile of the bioactive agent.

Another aspect of the current invention is a method of manufacturing a drug-polymer coated stent. FIG. 5 shows a flow diagram of one embodiment of a method of manufacturing a drug-polymer stent including a bioactive agent and a blended polymer of phenoxy and a styrenic block copolymer, in accordance with the present invention at 500. Drug-coated stent manufacturing method 500 comprises steps to form a drug-polymer solution containing the phenoxy polymers, the styrenic block copolymers, and one or more drugs or pharmaceutical compounds.

In this embodiment, a phenoxy resin or a phenoxy polymer is dissolved in a solvent to form a phenoxy polymer solution, as seen at block 510. The phenoxy polymer has a molecular weight, for example, between 20,000 Daltons and 200,000 Daltons. The phenoxy content in the phenoxy polymer is determined by the desired solids content, which may be less than 1 percent or as high as 5 percent by volume. The solvent is any suitable organic solvent capable of dissolving the phenoxy resin such as chloroform, tetrahydrofuran, methyl chloride, toluene, ethyl acetate or dioxane.

The styrenic block copolymer is mixed with the phenoxy polymer solution, as seen at block 520, to form a polymeric solution of phenoxy resin and styrenic block copolymer, as seen at block 530. The styrenic block copolymer may be added directly to the phenoxy polymer solution and mixed to form the polymeric solution. Alternatively, the styrenic block copolymer may be dissolved in a styrenic block copolymer solution comprising a suitable organic solvent such as chloroform, tetrahydrofuran, methyl chloride, toluene, ethyl acetate or dioxane, and then mixed with the phenoxy polymer solution to form the polymeric solution. The styrenic block copolymer has a molecular weight, for example, between 20,00 Daltons and 200,000 Daltons. The styrenic block copolymer content is usually less than 1 percent or as high as 5 percent by volume. The styrenic block copolymer typically comprises between 10 percent and 90 percent of the solids content in the polymer solution by volume. The phenoxy polymer may comprise between 10 percent and 90 percent of the solids content in the polymer solution by volume. The fractional percentage of the phenoxy polymer and the styrenic block copolymer provides a controlled drug-elution characteristic, and may be selected to provide a predetermined elution rate.

In this exemplary method of the present invention, one or more bioactive agents are mixed with the polymeric solution, as seen at block 540 to form a drug-polymer solution, as seen at block 550. The bioactive agents may be added directly into the polymeric solution and mixed to form the polymeric solution. Alternatively, the bioactive agents may be dissolved in a bioactive agent solution comprising a suitable solvent, then mixed with the polymeric solution to form the drug-polymer solution. In either case, a suitable amount of bioactive agent or drug is added to the drug-polymer solution. The drug constituency of the drug-polymer coating is usually between 0.5 percent and 50 percent of the bioactive drug by weight.

The drug-polymer solution is then applied to the stent framework and dried, as seen at block 560. The drug-polymer solution is applied by using an application technique such as dipping, spraying, painting or brushing. The drug-polymer solution is often dried by evaporating off the solvent after application at room temperature and under ambient conditions. A nitrogen or other controlled environment may also be used. Alternatively, the drug-polymer solution can be dried by evaporating the majority of the solvent at room temperature, then further dried the solution in a vacuum environment between room temperature of about 25 degrees centigrade and 45 degrees centigrade or higher to extract any pockets of solvent buried within the drug-polymer coating.

The thickness of the drug-polymer coating can vary, though is typically between 1 micron and 20 microns. Depending on the diameter and length of the stent, the weight of the drug-polymer coating is usually between 100 micrograms and 1500 micrograms for a range of stent sizes. Additional coats may be added to thicken the drug coating. A barrier coating or a primer may be disposed on the stent framework prior to coating with the drug-polymer to improve adhesion, particularly to metal stents such as stainless steel.

Variants of the method for manufacturing a drug-polymer coated stent can be used, such as mixing the constituents into the same solution, using different solvents for each component, or altering the order of mixing the stock solutions.

More specifically, illustrative examples of the present invention are provided herein.

EXAMPLE 1

Formulation of Blended Drug-Polymer Coating with Phenoxy Resin and Styrenic Block Copolymer A blended polymeric solution of phenoxy resin and styrenic block copolymers, with a pharmaceutical drug was formulated in a three-component procedure. An amount of phenoxy PKHC® from Phenoxy Specialties of Rock Hill, S.C., weighing 0.1510 grams was placed in a glass bottle and 10 milliliters of chloroform was added. The contents of the glass bottle were shaken until all the phenoxy was dissolved. An amount of Kraton-G® weighing 0.2159 grams was placed in a second glass bottle and 14.3 milliliters of chloroform was added. The contents of the glass bottle were shaken until the Kraton-G® was dissolved. An amount of anti-restenotic drug, such as an analog of rapamycin weighing 0.1554 grams, was placed in a third glass bottle and 10.3 milliliters of chloroform was added. The contents of the glass bottle were shaken until the entire drug was dissolved. A portion of the contents of the glass bottles were combined to obtain solutions with 1 percent solids content, the solids content comprising phenoxy, Kraton-G® and bioactive drug as seen in Table 1.

TABLE 1

Synthesis of Bioactive Drug and Blended Polymers of Phenoxy and Kraton-G ®

| Example Number | Solids (%) | Phenoxy | Kraton-G ® | Antirestenotic Drug |
|---|---|---|---|---|
| 1 | 1.0 | 1.2 mL | 1.8 mL | 1 mL |
| 2 | 1.0 | 0.9 mL | 2.1 mL | 1 mL |
| 3 | 1.0 | 0.6 mL | 2.4 mL | 1 mL |
| 4 | 1.0 | 0.3 mL | 2.7 mL | 1 mL |
| 5 | 1.0 | 0.15 mL | 2.85 mL | 1 mL |

The relative concentrations of components in the drug-polymer solutions corresponding to the examples in Table 1 are found in Table 2. All samples were successfully coated with the drug-polymer solutions.

TABLE 2

Fractional Components of Solids in Drug-Polymer Solutions

| Example Number | Phenoxy | Kraton-G ® | Antirestenotic Drug | P:K Ratio |
|---|---|---|---|---|
| 1 | 30% | 45% | 25% | 40:60 |
| 2 | 22.5% | 52.5% | 25% | 30:70 |
| 3 | 15% | 60% | 25% | 20:80 |
| 4 | 7.5% | 67.5% | 25% | 10:90 |
| 5 | 3.75% | 71.25% | 25% | 5:95 |

EXAMPLE 2

Elution of Antirestenotic Drugs from Stents with Blended Drug-Polymer Coatings

The elution of an antirestenotic drug from a biomedical stent coated with pharmaceutical drug and a blended polymeric solution of phenoxy resin and styrenic block copolymers was determined by insertion into a simulated biological environment. Measurements were made of the stent weight at predetermined intervals. One example of drug elution from a drug-polymer coated stent with 25% antirestenotic drug, 30% phenoxy, and 45% Kraton-G® is found in the plot of FIG. 3. All samples eluted the drug, the drug elution rate depending on the drug and the fractional portion of the phenoxy and Kraton-G®. Drug elution was also monitored with ultraviolet-visible spectroscopy (UV-VIS) and high-performance liquid chromatography (HPLC).

EXAMPLE 3

Simulated Lesion Abrasion Test of Stents with Blended Drug-Polymer Coatings

In this example, drug-polymer coated stents with blended drug-polymer coatings were tested to assess durability of the coated stents against simulated lesions. A silicon rubber tube with a small inner dimension was used to simulate lesions by passing the coated stent multiple times through the tube. A stent was then deployed and inspected with an SEM. All phenoxy and Kraton-G® coated stents passed the simulated lesion abrasion test.

EXAMPLE 4

Cytotoxicity Studies of Stents with Blended Drug-Polymer Coatings

In this example, drug-polymer coated stents with blended drug-polymer coatings were tested for potential cytotoxicity. The tests were conducted in accordance with International Standards Organization ISO 10993-5 and United States Pharmacopeia USP 24 section 87. In vitro tests conducted on metal coupons coated with the blended polymeric coating of phenoxy and Kraton-G® showed no evidence of cell toxicity after 24 hours.

EXAMPLE 5

Hemolysis Studies of Stents with Blended Drug-Polymer Coatings

Hemolysis studies were carried out on phenoxy/Kraton-G® drug-polymer coated stents with positive controls of 0.1 percent sodium carbonate in sterile water and negative controls of polypropylene pellets. All were contacted with rabbit blood and incubated at 37 degrees centigrade for one hour. The results indicated 0 percent hemolysis for the phenoxy or Kraton samples.

Another aspect of the present invention is a method of treating a vascular condition. FIG. 6 shows a flow diagram of one embodiment of a method of treating a vascular condition, in accordance with the present invention at 600.

In this embodiment, one or more bioactive agents or drugs are selected along with the fractional constituencies of the polymeric blend of phenoxy and styrenic block copolymer to achieve an intended pharmaceutical intent such as a predetermined elution rate of the bioactive agent, as seen at block 610.

A drug-polymer coated stent is fabricated with the selected polymeric blend and bioactive agents, as seen at block 620. The stent is coated with the drug-polymer coating, and dried. The drug-polymer coating includes a bioactive agent and a polymeric blend of a phenoxy polymer and a styrenic block copolymer. In this exemplary method, finished coated stents are reduced in diameter and placed into the distal end of the catheter, in a process that forms an interference fit, which secures the stent onto the catheter. The catheter with the stent may be placed in a catheter package and sterilized prior to shipping and storing. Sterilization of the stent using conventional means is completed before clinical use.

When ready for deployment, the drug-polymer coated stent including a bioactive agent and the selected polymeric blend is inserted into a vessel of the body, as seen at block 630. The drug-coated stent is inserted typically in a controlled environment such as a catheter lab or hospital. The stent is deployed, for example, by expanding the stent with a balloon or by extracting a sheath to allow a self-expandable stent to enlarge after positioning the stent at a desired location within the body.

Once deployed, the drug-polymer coating on the stent framework is eluted into the body and particularly into the tissue bed surrounding the stent framework, as seen at block 640. The elution rate of the bioactive agent into the body is based on the fractional constituency of the polymeric blend and the selected bioactive agents, among other factors.

Although the present invention applies to cardiovascular and endovascular stents with timed-release pharmaceutical drugs, the use of polymeric blends of phenoxy polymer and styrenic block copolymers in polymer-drug coatings and polymer coatings may be applied to other implantable and blood-contacting biomedical devices such as coated pacemaker leads, microdelivery pumps, feeding and delivery catheters, heart valves, artificial livers and other artificial organs.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vascular condition, comprising:
   a catheter;
   a stent coupled to the catheter, the stent including a stent framework;
   a drug-polymer coating disposed on the stent framework, wherein the drug-polymer coating comprises a polymeric blend of a phenoxy polymer and a styrenic block copolymer; and
   a bioactive drug dispersed within the drug-polymer coating,
   wherein the styrenic block copolymer is selected from the group consisting of styrene-ethylene/butylene-styrene, styrene-ethylene/propylene-styrene, styrene-butadiene-styrene and styrene-isoprene-styrene.

2. The system of claim 1 wherein the catheter includes a balloon used to expand the stent.

3. The system of claim 1 wherein the catheter includes a sheath that retracts to allow expansion of the stent.

4. The system of claim 1 wherein the stent framework comprises a metallic base.

5. The system of claim 4 wherein the metallic base is selected from the group consisting of stainless steel, nitinol, tantalum, MP35N alloy, platinum, titanium, a suitable biocompatible alloy, a suitable biocompatible material, and a combination thereof.

6. The system of claim 1 wherein the stent framework comprises a polymeric base.

7. The system of claim 1 wherein the phenoxy polymer has a molecular weight between 20,000 Daltons and 200,000 Daltons.

8. The system of claim 1 wherein the styrenic block copolymer has a molecular weight between 20,000 Daltons and 200,000 Daltons.

9. The system of claim 1 wherein the polymeric blend provides a controlled drug-elution characteristic.

10. The system of claim 1 wherein the polymeric blend comprises between 10 percent and 90 percent phenoxy polymer by volume.

11. The system of claim 1 wherein the polymeric blend comprises between 10 percent and 90 percent styrenic block copolymer by volume.

12. The system of claim 1 wherein the drug-polymer coating comprises between 0.5 percent and 50 percent of the bioactive drug by weight.

13. The system of claim 1 wherein the drug-polymer coating has a thickness between 1 micron and 20 microns.

14. The system of claim 1 wherein the drug-polymer coating has a weight between 100 micrograms and 1500 micrograms.

15. The system of claim 1 wherein the bioactive drug comprises an antirestenotic agent.

16. The system of claim 1 wherein the bioactive drug comprises a bioactive agent.

17. The system of claim 16 wherein the bioactive agent is selected from a group consisting of an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

18. A drug-polymer coated stent, comprising:
    a stent framework; and
    a drug-polymer coating disposed on the stent framework, wherein the drug-polymer coating comprises a polymeric blend of a phenoxy polymer and a styrenic block copolymer, with a bioactive drug dispersed within the drug-polymer coatings,
    wherein the styrenic block copolymer is selected from the group consisting of styrene-ethylene/butylene-styrene, styrene-ethylene/propylene-styrene, styrene-butadiene-styrene and styrene-isoprene-styrene.

19. The drug-polymer coated stent of claim 18 wherein the stent framework comprises one of a metallic base or a polymeric base.

20. The drug-polymer coated stent of claim 18 wherein the polymeric blend comprises a fractional part of the styrenic block copolymer based on a predetermined elution rate of the bioactive drug.

21. The drug-polymer coated stent of claim 20 wherein the fractional part of the styrenic block copolymer is between 10 percent and 90 percent.

22. The drug-polymer coated stent of claim 18 wherein the bioactive drug comprises a bioactive agent selected from the group consisting of an antirestenotic agent, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

* * * * *